(12) United States Patent
Drasler et al.

(10) Patent No.: US 9,254,124 B2
(45) Date of Patent: Feb. 9, 2016

(54) SELF-ORIENTATING SUTURE WOUND CLOSURE DEVICE

(75) Inventors: William J. Drasler, Minnetonka, MN (US); Tracee Eidenschink, Wayzata, MN (US); Joseph M. Thielen, Buffalo, MN (US); Mark L. Jenson, Greenfield, MN (US); Anu Sadasiva, Maple Grove, MN (US)

(73) Assignee: BOSTON SCIENTIFIC SCIMED INC., Maple Grove, MN (US)

( * ) Notice: Subject to any disclaimer, the term of this patent is extended or adjusted under 35 U.S.C. 154(b) by 1561 days.

(21) Appl. No.: 12/026,207

(22) Filed: Feb. 5, 2008

(65) Prior Publication Data

US 2008/0312667 A1 Dec. 18, 2008

Related U.S. Application Data

(60) Provisional application No. 60/888,208, filed on Feb. 5, 2007.

(51) Int. Cl.
*A61B 17/04* (2006.01)
*A61B 17/00* (2006.01)
*A61B 17/34* (2006.01)
*A61B 19/00* (2006.01)

(52) U.S. Cl.
CPC ......... *A61B 17/0057* (2013.01); *A61B 17/0469* (2013.01); *A61B 2017/00641* (2013.01); *A61B 2017/00663* (2013.01); *A61B 2017/00867* (2013.01); *A61B 2017/047* (2013.01); *A61B 2017/0472* (2013.01); *A61B 2017/3484* (2013.01); *A61B 2019/467* (2013.01); *A61B 2019/4857* (2013.01)

(58) Field of Classification Search
CPC ........... A61B 17/0057; A61B 17/0469; A61B 2017/00663; A61B 2017/00641; A61B 2017/00672; A61B 2017/047; A61B 2017/0469; A61B 2017/0472; A61B 2019/0467
USPC ................. 606/139, 144, 148, 157, 158, 213, 606/140–143, 151, 214–216, 232
See application file for complete search history.

(56) References Cited

U.S. PATENT DOCUMENTS

| | | | | |
|---|---|---|---|---|
| 5,593,422 | A | * | 1/1997 | Muijs Van de Moer et al. ............... 606/213 |
| 5,755,727 | A | * | 5/1998 | Kontos .......................... 606/144 |
| 5,810,849 | A | * | 9/1998 | Kontos .......................... 606/144 |

(Continued)

FOREIGN PATENT DOCUMENTS

WO 2006/124251 A2 11/2006

*Primary Examiner* — Alexander Orkin
(74) *Attorney, Agent, or Firm* — Seager, Tufte & Wickhem LLP

(57) ABSTRACT

A device is disclosed for providing an indication as to the relative position of a vessel or artery opening thereby facilitating the choice of which several closure techniques to use. A disclosed device includes an outer tube and a collapsible foot slidably disposed within a distal end of the outer tube. The device may further include one or more threaded suture needles, a biodegradable plug or other wound closing device that is connected to another shaft. The collapsed or folded foot is pushed distally out of the tube and through the opening in the vessel whereupon the foot expands. Pulling the expanded foot in the proximal direction provides an indication as to the orientation of the opening in the vessel, which assists in determining the type of closing procedure to be carried out.

23 Claims, 6 Drawing Sheets

(56) References Cited

U.S. PATENT DOCUMENTS

| | | | |
|---|---|---|---|
| 6,056,768 A * | 5/2000 | Cates et al. | 606/213 |
| 6,368,341 B1 | 4/2002 | Abrahamson | |
| 6,780,197 B2 * | 8/2004 | Roe et al. | 606/213 |
| 2002/0072768 A1 | 6/2002 | Ginn | |
| 2005/0085856 A1 | 4/2005 | Ginn | |
| 2005/0121042 A1 * | 6/2005 | Belhe et al. | 128/887 |
| 2006/0264978 A1 * | 11/2006 | Belhe et al. | 606/150 |
| 2008/0312684 A1 * | 12/2008 | Drasler et al. | 606/213 |

* cited by examiner

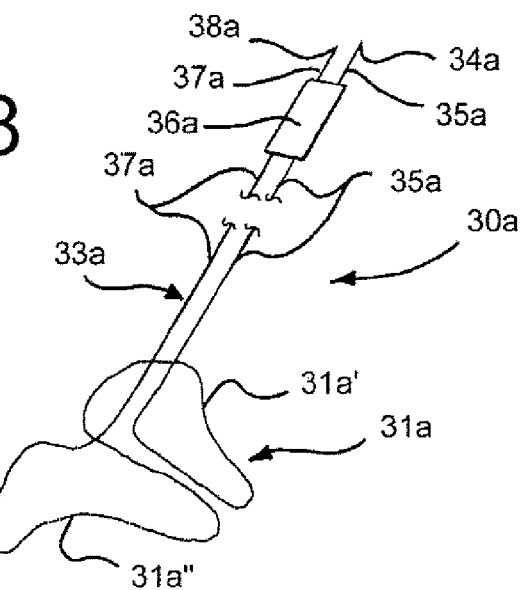
FIG. 8
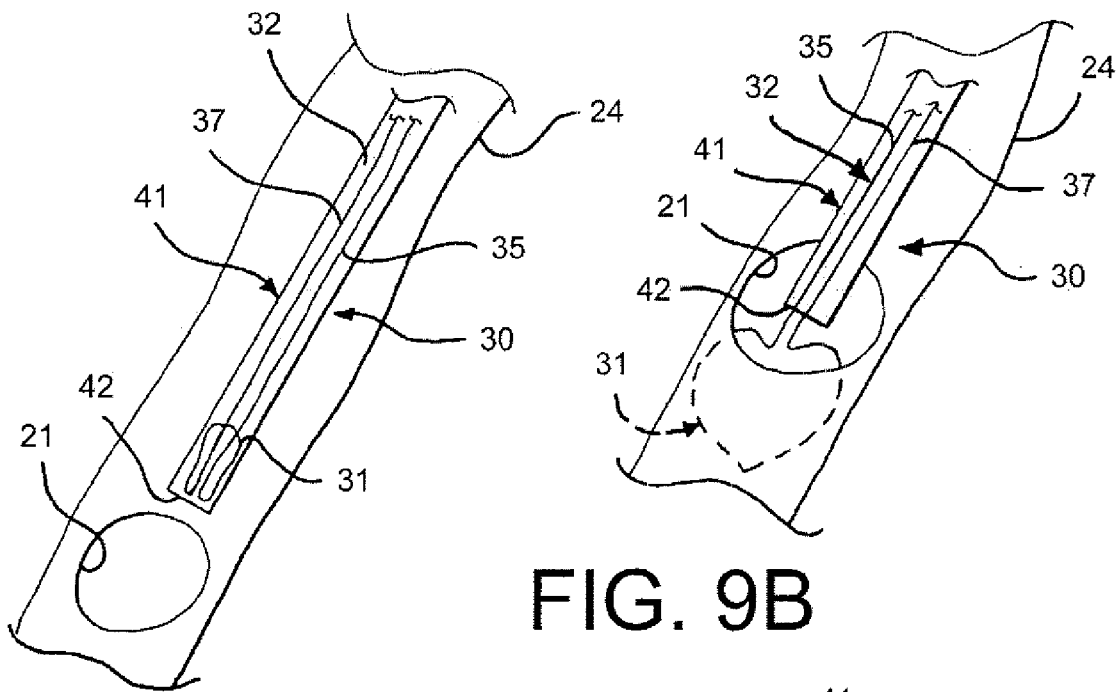
FIG. 9A
FIG. 9B
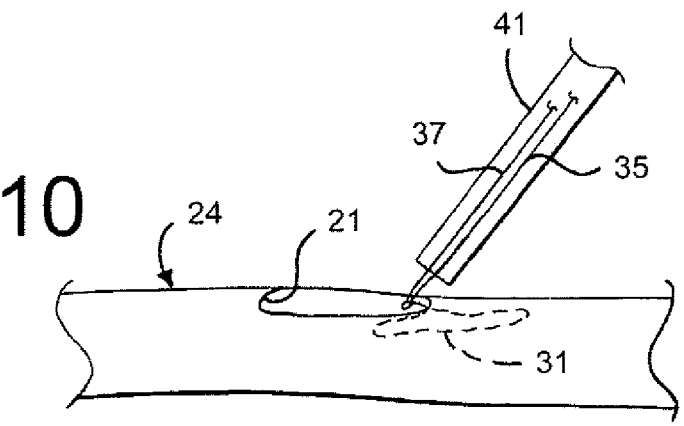
FIG. 10

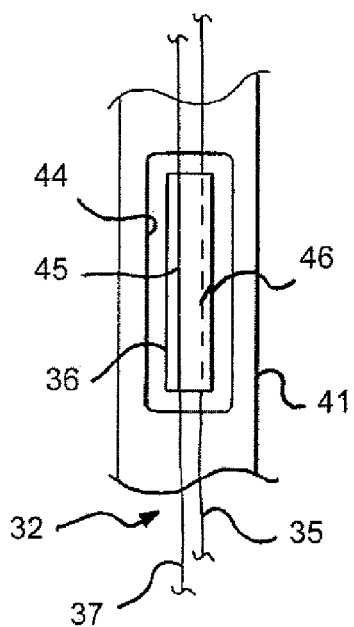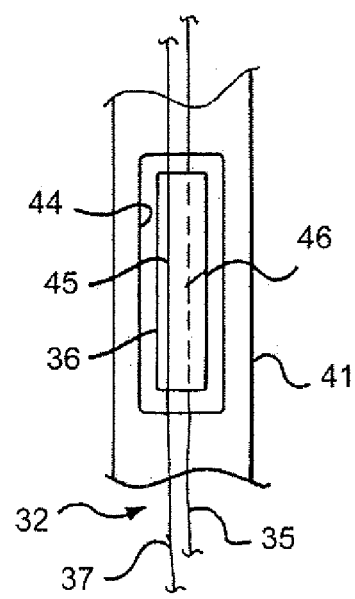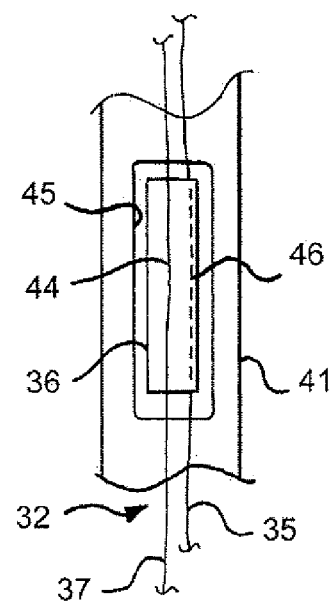
FIG. 11  FIG. 12  FIG. 13
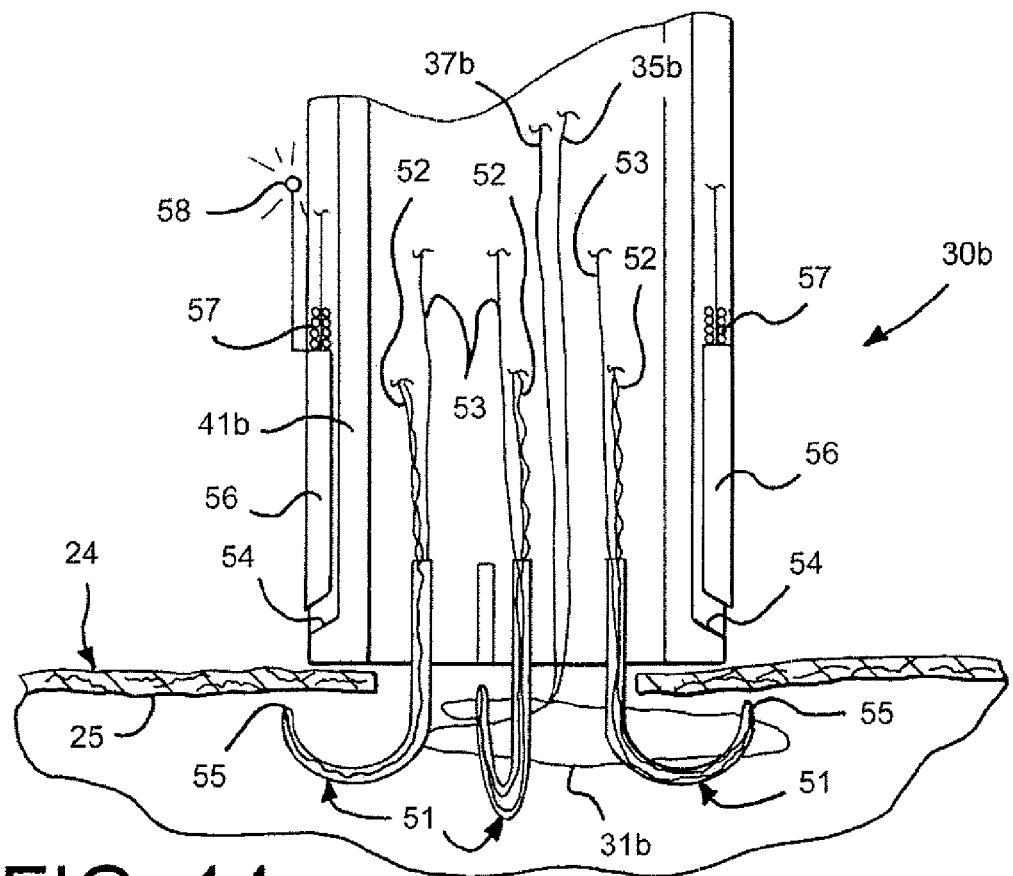
FIG. 14

SELF-ORIENTATING SUTURE WOUND CLOSURE DEVICE

CROSS-REFERENCE TO RELATED APPLICATION

This application is a non-provisional patent application claiming priority under 35USC§119(e) to U.S. provisional patent application Ser. No. 60/888,208 filed on Feb. 5, 2007

FIELD OF THE DISCLOSURE

Methods and apparatuses are disclosed for determining the orientation of a vascular opening on the vessel and thereafter closing said vascular opening. More specifically, systems and methods are disclosed for accurately determining the location of a vascular opening on the vessel so that the appropriate closure technique is employed such as the appropriate suturing technique or plug or pledget technique.

BACKGROUND OF THE DISCLOSURE

Various surgical procedures are performed by medical specialists such as cardiologists and radiologists, utilizing percutaneous entry into a blood vessel. To facilitate cardiovascular procedures, a needle is introduced through the skin and into a target blood vessel, often the femoral artery. The needle forms a puncture through the blood vessel wall at the distal end of a tract that extends through the overlying tissue A guide wire is introduced through a bore of the needle before the needle is withdrawn over the guide wire. An introducer sheath is next advanced over the guide wire. The sheath and guide wire are left in place to provide access during subsequent procedures.

The sheath facilitates passage of a variety of diagnostic and therapeutic instruments and devices into the vessel and its tributaries. Such diagnostic procedures may include angiography, intravascular ultrasonic imaging, and the like. Typical interventional procedures include angioplasty, atherectomy, stent and graft placement, embolization, and the like. After a procedure is completed, the catheters, guide wire, and introducer sheath are removed, and it is necessary to close the vascular puncture to provide hemostasis and allow healing The common technique for achieving hemostasis is to apply pressure, either manually or mechanically, on the patient's body in the region of the tissue tract and vascular puncture. Typically, pressure is applied manually and subsequently is maintained through the use of mechanical clamps and other pressure-applying devices. While effective in most cases, the application of external pressure to the patients skin presents a number of disadvantages. For example, when applied manually, the procedure is time-consuming and requires the presence of a medical professional for thirty minutes or more. For both manual and mechanical pressure application, the procedure is uncomfortable for the patient and frequently requires the administration of analgesics to be tolerable.

Moreover, complications from manual pressure application are common The application of excessive pressure can occlude the underlying artery, resulting in ischemia and/or thrombosis. Even after hemostasis has apparently been achieved, the patient must remain immobile and under observation for hours to prevent dislodgment of the clot and to assure that bleeding from the puncture wound does not resume. Renewed bleeding through the tissue tract is not uncommon which can result in hematoma, pseudoaneurisms, and arteriovenous fistulas. Such complications may require blood transfusion, surgical intervention, or other corrective procedures. The risk of these complications increases with the use of larger sheath sizes, which are frequently necessary in interventional procedures, and when the patient is anticoagulated with heparin or other drugs.

As a result, several alternatives to the manual pressure hemostasis technique have been proposed to address the problem of sealing the opening in vessel wall following percutaneous transcatheter procedures. For example, bioabsorbable, thrombogenic plugs comprising collagen and other materials have been used at the vessel wall opening to stop bleeding. These large hemostasis plugs stimulate blood coagulation at the vessel opening. Other techniques provide for the use of small dissolvable disks or anchors that are placed in the vessel to block or clamp the opening.

Additional techniques use needles and sutures to ligate the opening. The needle is and sutures are delivered through a catheter Obviously, any suturing procedure carried out through a catheter or tube requires a high level of skill.

Another technique involves the injection of a procoagulant into the opening with a balloon catheter blocking inside the vessel lumen. However, it is possible for the clotting agent to leak past the balloon into the vessel lumen and cause stenosis.

Lasers and radio-frequency (RF) energy have also been used to thermally fuse or weld the punctured tissue together. Other more recent techniques involve the use of high frequency ultrasound (HIFU) energy.

While all of the above procedures have advantages and disadvantages, no current procedure addresses the problem of informing the physician of the orientation of the opening on the vessel. Specifically, the operating physician typically does not know whether the needle that penetrates the vessel wall penetrated the vessel at the top, towards the right side of the vessel or towards the left side of the vessel (from the physician's perspective or from a top view). Knowledge of the orientation of the opening in the vessel would be beneficial for purposes of deciding which closure technique to employ Referring to figures and 1-5, it would be beneficial for the physician to know whether (a) the opening passes through a top area of the vessel 24 as shown by the opening 21 of FIGS. 1, 2 and 4, or whether (b) the opening passes through either a right side of the vessel 24 as shown by the opening 22 of FIGS. 1, 2 and 5, or (c) whether the opening passes through a left side of the vessel 24 as shown by the opening 23 of FIGS. 1, 2 and 3. The orientation of the opening 21, 22 or 23, from the physician's top view of the vessel or artery 24, would be a factor in determining the correct closure technique. Specifically, certain closure techniques may be appropriate for a top orientation (or "top stick") but not appropriate for side orientations (or "side sticks") In summary, deciding between sutures, a plug, RF or HIFU may depend upon orientation of the opening.

Accordingly, there is a need for devices and methods for determining the orientation of a vascular opening created during an intravascular procedure so that the appropriate closure technique may be utilized upon completion of the intravascular procedure.

SUMMARY OF THE DISCLOSURE

In satisfaction of the aforenoted needs, devices are disclosed for determining an orientation of an opening in a vessel or artery for purposes of this disclosure, all orientations, e.g. top, right and left, are taken from a top plan view of a vessel or artery, or the physician's view looking downward on the vessel.

One disclosed device comprises an outer tube and a collapsible foot slidably disposed within a distal end of the outer tube. The foot is connected to a shaft which passes through the tube and exits a proximal end of the tube. The foot may be pushed distally out of the tube and through the opening in the vessel where it expands. After the expansion, the operator pulls the expanded foot in the proximal direction against the interior vessel wall. As the foot engages the interior vessel wall, the foot will twist or rotate. In the twisting of the foot, rotation is translated up the shaft, which may include markings that provide an indication as to the orientation of the opening in the vessel In a refinement, the foot is heart shaped In another refinement, the foot and shaft are made from a single piece of wire. Preferably, the wire is an alloy with a shape memory. Suitable shape memory alloys are known to those skilled in the art, examples of which are found in art related to the construction of expandable stents such as a nickel-titanium alloys including Nitinol®, and cobalt-chromium-nickel alloys including Elgiloy®. Alternatively, materials not generally considered "shape-memory" may be used, especially those having considerable elastic properties, including certain stainless steels, spring materials, other highly elastic materials, polymers or composites. Also, a suitable structure can be made from multiple materials, where one material has a highly elastic property.

In another refinement, the foot and shafts are made from polymers such as nylon, PEEK, Pebax® (polyether block amide), Teflon® (polytetrafluoroethylene (PTFE)) or acetal such as polyacetal, polyoxymethylene (POM) or polyformaldehyde.

In a related refinement, the wire comprises a first proximal end connected to a first shaft section connected to the foot that is connected to a second shaft section terminating at a second proximal end.

In a refinement, the shaft is connected to an indicator bar that provides an indication as to the orientation, i.e., left, top or right, of the opening. In a related refinement, the indicator bar has indicia marked thereon for indicating a first position of the foot when the opening is disposed on a left side of the vessel, a second position of the foot when the opening is disposed on a top of the vessel and a third position of the foot when the opening is disposed on a right side of the vessel.

In a related refinement, the outer tube has a window disposed towards a proximal end thereof and the indicator bar is positioned in alignment with the window so the indicia can be seen through the window. The "tube" may be a catheter, such as an introduction catheter In a refinement, the tube accommodates a suturing mechanism. In a related refinement, the suturing mechanism comprises a plurality of threaded hook needles connected to or engaged by shafts for manipulating the position and movement of the needles.

In a refinement, the tube accommodates a plug, e.g., a bioabsorbable plug, for closing the opening Materials used for constructing such a plug are known to those skilled in the art.

In a refinement, the tube comprises two coaxial tubes wherein the inner tube holds the plug in the opening while the external tube is withdrawn In a refinement, a disclosed device comprises an outer tube and a collapsible foot slidably disposed within a distal end of the outer tube The foot is connected to a first shaft that passes through the tube and exits a proximal end thereof. The device further comprises a threaded suture needle that is connected to a second shaft. The collapsed or folded foot may be pushed distally out of the tube and through the opening in the vessel whereupon the foot expands. Pulling the expanded foot in the proximal direction (i.e., pulling the shaft connected to the foot towards the proximal end of the tube or catheter) results in a twisting of the foot as it engages the vessel wall which provides an indication as to the orientation of the opening in the vessel, which can dictate or determine the type of suturing procedure.

In another refinement, a disclosed device comprised the collapsible or folded foot connected to a first shaft as well as a biodegradable plug connected to a second shaft.

In a refinement, the indicator bar provides notice to the operator or physician that the opening is in one of three positions-left, top or right. Accordingly, the indicator bar should have at least two indicia marked thereon (one indicia may be "blank") for indicating the left, top and right positions. As an alternative, the indicator bar may indicate a relative position in degrees, mm or µm in deviation from a top stick (or top position).

Methods are disclosed for determining an orientation of an opening in a vessel wall. One disclosed method comprises inserting a device through a channel leading to the opening in the vessel. The device comprises an outer tube with a collapsible foot slidably disposed within a distal end of the outer tube as described above. The method further comprises applying a distally directed force to the shaft to push the foot through the opening or sheath, allowing the foot to expand in the vessel, applying a proximally directed force to the shaft to pull the expanded foot against the vessel wall, and viewing the indicator bar and determining if the opening is disposed on the left, top or right side of the vessel.

In a refinement, the method comprises causing the foot to rotate or twist as it engages the interior vessel wall which thereby causes the indicator bat to twist or rotate and viewing of the movement of the indicator bar is used to determine if the opening is disposed on the left, top or right side of the vessel from the physician's viewpoint.

In another refinement, a small thread can be attached to the tip of the heart-shaped foot so when a suture or plug is inserted, the foot can be withdrawn. Specifically, a proximally directed tug on this thread collapses the foot thereby enabling it to be removed from the vessel Removal of the foot is important and the "heart" shape of this embodiment lends itself to collapsability and therefore removability from the vessel In a Refinement, the method further comprises suturing the opening with a suturing mechanism disposed in the outer tube.

In another refinement, the method further comprises plugging the opening with a bioabsorbable plug accommodated in the outer tube Other advantages and features will be apparent from the following detailed description when read in conjunction with the attached drawings.

BRIEF DESCRIPTION OF THE DRAWINGS

For a more complete understanding of the disclosed methods and apparatuses, reference should be made to the embodiment illustrated in greater detail on the accompanying drawings, wherein:

FIG. 8 is a perspective view of yet another indicating device;

FIGS. 9A and 9B are top perspective views of the indicating device and catheter or outer tube shown in FIG. 6 passing towards and through an opening respectively with FIG. 9B showing the location of the indicating device disposed against an interior surface of the vessel wall after its expansion;

FIG. 10 is a side view of the indicating device and catheter as shown in FIGS. 9A-9B;

FIG. 11 is a partial plan view of a catheter section with a window disposed therein and a position indicator that comprises part of a disclosed vessel opening orientation indicating device, wherein the position indicator indicates that the vessel opening has a top orientation;

FIG. 12 is another partial plan view of the catheter section and position indicator shown in FIG. 11, but wherein the position indicator indicates that the vessel opening has a left side orientation;

FIG. 13 is another partial plan view of the catheter section and position indicator shown in FIGS. 11 and 12, but wherein the position indicator indicates that the vessel opening has a right side orientation;

FIG. 14 is a schematic illustration of a disclosed vessel opening orientation indicating device incorporated into a suturing device wherein the indicator and suturing needles are disposed inside the vessel;

It should be understood that the drawings are not necessarily to scale and that the disclosed embodiments are sometimes illustrated diagrammatically and in partial views. In certain instances, details which are not necessary for an understanding of the disclosed methods and apparatuses or which tender other details difficult to perceive may have been omitted. It should be understood, of course, that this disclosure is not limited to the particular embodiments illustrated herein

DETAILED DESCRIPTION

Figure 1:
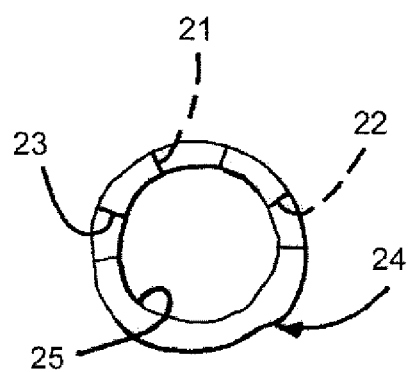
FIG. 1 is an end sectional view of a vessel illustrating three different orientations of a vessel opening created during an intravascular procedure including top, right side and left side orientations.
Figure 2:
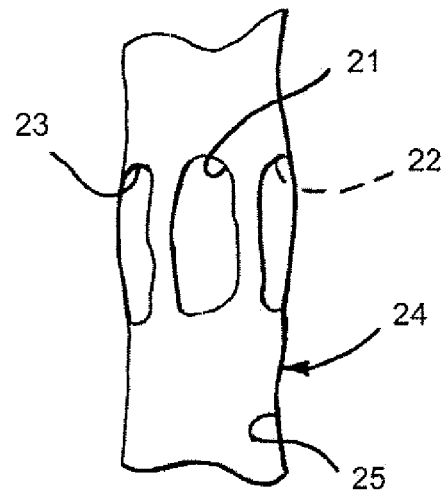
FIG. 2 is a partial top plan view of the vessel shown in FIG. 1.
Figure 3:
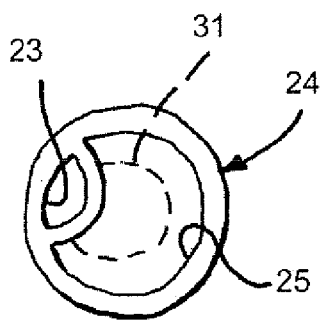
FIG. 3 is a sectional and perspective view of a vessel with an opening having a left side orientation or "left stick" opening.
Figure 4:
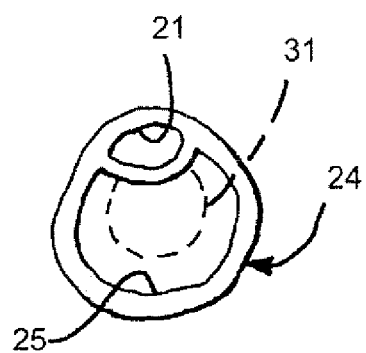
FIG. 4 is a sectional and perspective view of a vessel with an opening having a top side orientation or "top stick" opening.
Figure 5:
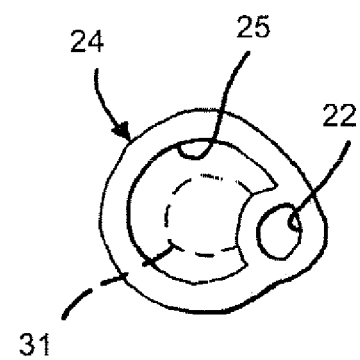
FIG. 5 is a sectional and perspective view of a vessel with an opening having a right side orientation or "right stick" opening.
Figure 6A:
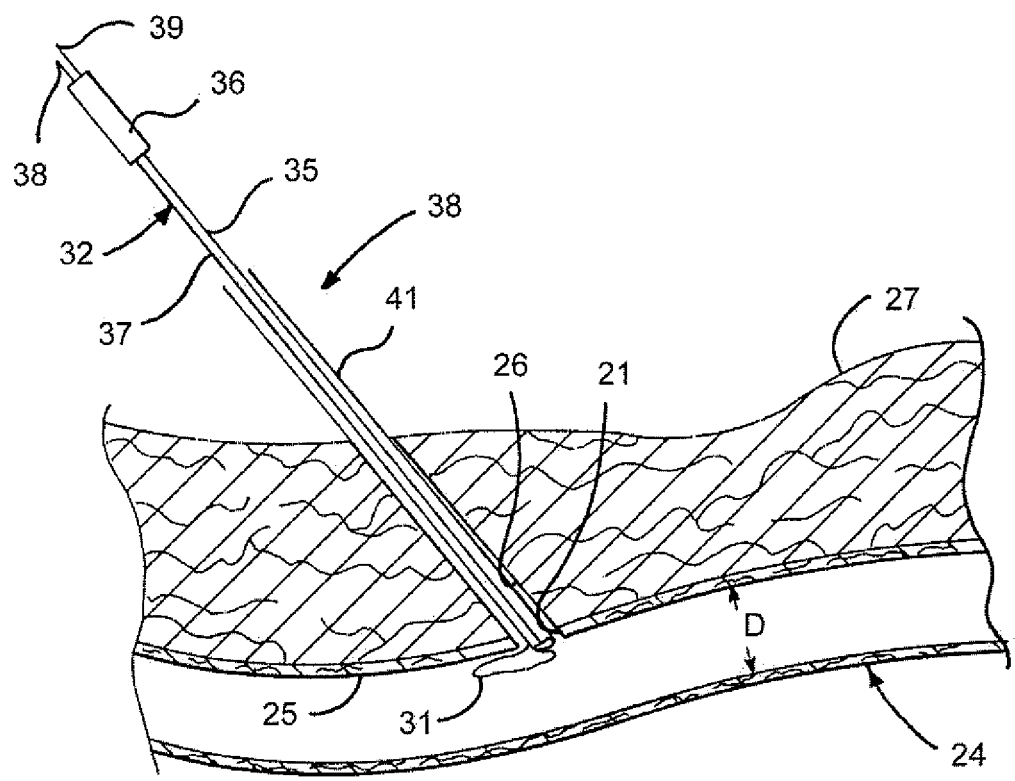
FIG. 6A is a sectional view of a section of a body, illustrating a catheter and opening orientation indicating device extending through a puncture that extends transdermally into the vessel having an internal diameter D.

FIG. 6A illustrates one use for the devices and methods disclosed herein. A patient's skin is shown at 27 with a channel 26 extending therethrough to the vessel 24 In opening 21 has been made in the vessel 24 through which an intravascular procedure has been carried out. As shown in greater detail below in connection with FIGS. 7-10, the device 30 has been inserted through the channel 26 and a collapsible wile foot 31 has been pushed out of a tube 41 into the vessel 24, allowed to expand, and subsequently pulled proximally against the vessel wall 25 The position that the foot 31 assumes against the vessel wall 25 indicates to the physician the general orientation of the opening 21. In the case as shown in FIG. 6A, the opening 21 is along the top side of the vessel 24 or is classified as a "top stick." When the foot 31 is pulled up against the interior vessel wall 25 in general alignment with the vessel 24, the foot 31 will have twisted or rotated to achieve the position shown in FIG. 6A and this movement is translated to the physician by way of the shaft 32 or indicator bar 36 which is connected to the shaft 32. The shaft 32 may comprise one or more shaft sections 35, 37 connected to the foot 31 (see FIG. 7). FIGS. 3-5 also show a foot 31 in general alignment with the vessel 24 thereby indicating predictability of the twisting of the foot 31 and shaft 32 as the foot 31 is located in the vessel 24 and pulled in a proximal direction so that the foot 31 is in general alignment with the vessel 24 as shown in FIG. 6A.

Figure 6B:
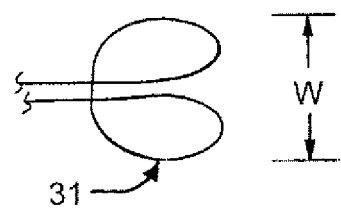
FIG. 6B is a partial view of the "foot" of the opening orientation indicating device particularly illustrating the width W of said foot.

FIG. 6A also indicates a diameter D of the vessel 24. This dimension is in contrast to the width W for the foot 31 shown in FIG. 6B. The width W of the foot 31 should be less than the diameter D of the vessel 24. Preferably, the width W should range from about 0.5 D to about 0.75 D preferably from about 0.6 D to about 0.7 D, most preferably about 0.66 D.

Figure 7A:
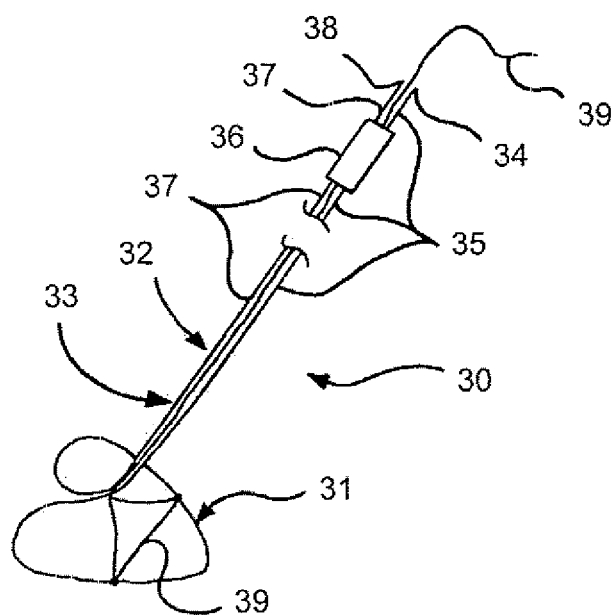
FIG. 7A is a perspective view of the indicating device like the one shown in FIG. 6A, illustrating one retraction mechanism.

FIG. 7A illustrates the probe-like device 30 that includes the heart-shaped foot 31 connected to the shaft 32 that comprises a pair of distally extending wire sections More specifically, the device 30 of FIG. 7A is fabricated from a single piece of shape memory wire 33 with a first proximal end 34 connected to a first shaft section 35 that, as shown in FIG. 7A, passes through or is otherwise attached to the indicator bar 36. The function and operation of the indicator bar 36 will be described in greater detail below in connection with FIGS. 11-13. Returning to FIG. 7A, the first shaft section 35 is connected to the foot 31 which, in turn, is connected to a second shaft section 37 that terminates at a second proximal end 38 and that also passes through the indicator bar 36

Figure 7B:
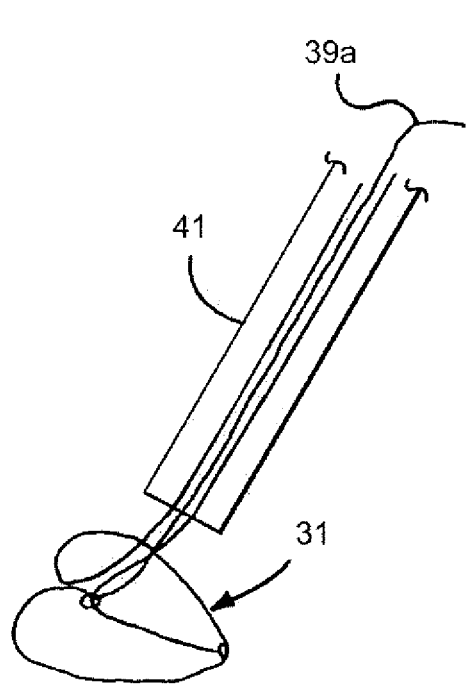
FIG. 7B is a perspective view of another opening indicating orientation device like the device shown in FIG. 6A, illustrating another retraction mechanism.
Figure 7C:
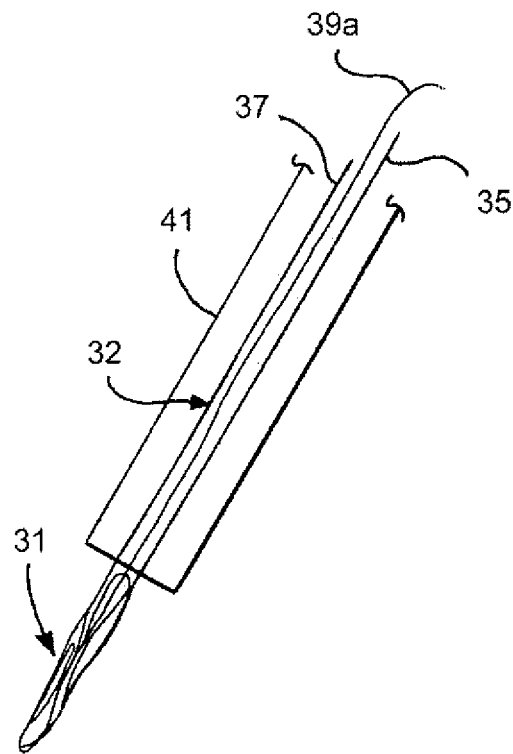
FIG. 7C is a perspective view of the indicating device shown in FIG. 6A in a collapsed position.

FIG. 7A also illustrates the employment of a string or thread 39 is coupled to the foot 31 and that extends upward along the shaft 32. The string 39 is used to collapse the foot 31 prior to its removal from the vessel 24. Another scheme for connecting the string 39a to a foot 31 is illustrated in FIG. 7B. The string 39a is coupled to the "point" of the heart-shaped foot 31. The collapsed foot 31 is illustrated in FIG. 7C Removability of the foot 31 from the vessel 24 is important and the collapsability/expandability/re-collapsability feature of the disclosed vessel opening orientation device 30 satisfies this concern The foot 31 of FIG. 7A is heart-shaped, although other shapes can be utilized. For example, referring to FIG. 8, the foot 31a includes two symmetrical halves 31a', 31a" formed from a single piece of wire 33a. Similar to the embodiment 30 of FIG. 7, the wire 33a of the device 30a of FIG. 8 includes a first proximal end 34a that is connected to a first shaft section 35a which, in turn, is connected to the foot half 31a' which is connected to the second foot half 31a". The second foot half 31a", in turn, is connected to the second shaft section 37a, which terminates at the second proximal end 38a. The shaft portions 35a and 37a both pass through the indicator bar 36a as shown FIGS. 9A and 9B illustrate the device 30 of FIGS. 6 and 7 with an accompanying outer tube 41 that includes a distal end 42 through which the foot 31 extends In an initial position as shown in FIG. 9A, the foot 31 is folded and accommodated proximally of the distal end 42 of the tube 41. The tube 41 and device 30 are shown schematically as a tube 41 is being moved towards the opening 21 in the vessel 24. When the tube 41 is in position inside the opening 21, as shown in FIG. 9B, force is applied to the shaft or shaft portions 35, 37 of the device 30 in a distal direction (or towards the opening 43) and the foot 31 is pressed outward from the tube 41 and into the vessel 44 through the opening 21 whereupon the foot 31 expands as shown in FIG. 9B Returning to FIGS. 6 and 10, after the foot 31 has as expanded in the vessel 24, it can be pulled in the proximal direction and up against the interior wall 25 of the vessel 24 where it will rotate to the general position shown in FIG. 6. The rotation of the foot 31 is translated to the indicator bar 36 (FIGS. 6 and 7) which, in turn, provides an indication to the physician or operator as to the orientation of the opening 21. In other words, one type of rotation will indicate that the opening is a left stick, an other type of rotation will indicate that the opening is a top stick and another type of rotation will indicate that the opening is a right stick, all of which can be indicated using the simple indicator bar 36 or another type of indicating device as discussed below.

Turning to FIGS. 11-13, one type of indicator bar 36 that may be employed in with the disclosed devices is illustrated. The bar or block 36 is mounted on the shaft portion 32 of the device 30 which, in this case, includes the wire shaft sections 35, 37. The block 36 may be visible to an operator or physician through a window 44 in the outer tube or sheath 41. The block 36 preferably includes two or mole indicia shown in FIGS. 11-13 at 45, 46. By way of example only, FIG. 11 could illustrate a situation where the opening 21 is in the top position or "top stick" position with both indicia 45, 46 clearly visible to the operator through the window 44 FIG. 12 could illustrate, for example, a "left stick" position with the solid line indicia 45 disposed towards the left and the dashed line indicia 46 disposed towards the center of the window 44 FIG. 13, for example, could illustrate a "right stick" position with the solid line indicia 45 centered in the window 44 and the dashed line indicia 46 towards the light side of the window 44. Obviously, numerous variations of this scheme can be employed and still fall within the spirit and scope of this disclosure. As another example, the indicia may indicate a degree of non-centeredness of the opening of wound in the vessel 24 such as a series of markings indicating the degree of the off-center position of the opening, either to the left or to the right.

Turning to FIG. 14, a more complex device 30b is disclosed which includes a foot 31b disposed inside a vessel 24. In addition to the foot 31b and shaft portions 35b, 37b, the outer tube 41b may also include a suturing mechanism such as a plurality of needles, in this case a plurality of hook-shaped needles 51 with accompanying thread or suture material 52 and equipped with a push bar or shaft 53. The other tube 41b may also be equipped with slots 54 for accommodating the tips 55 of the needles 51 as well as a lock mechanism 56 to secure the needles 51 in place in the slots 54. The lock mechanisms 56 may be spring biased as shown by the springs 57 and an indicator light 58 or other indication means such as flags, alignment markings, audible sounds, other visible indicia, etc may be employed to indicate to the physician when a needle 51 has either been secured in a slot 54 or has been removed or dislodged from a slot 54. Other arrangements of needles and slots, or other grasping mechanisms as alternative to the slots could be used. For example, various numbers of needles, needles poking in from the outside of the vessel, interference fit tubes to grasp the needles, and so forth, while still utilizing the alignment features disclosed herein.

Figure 15:
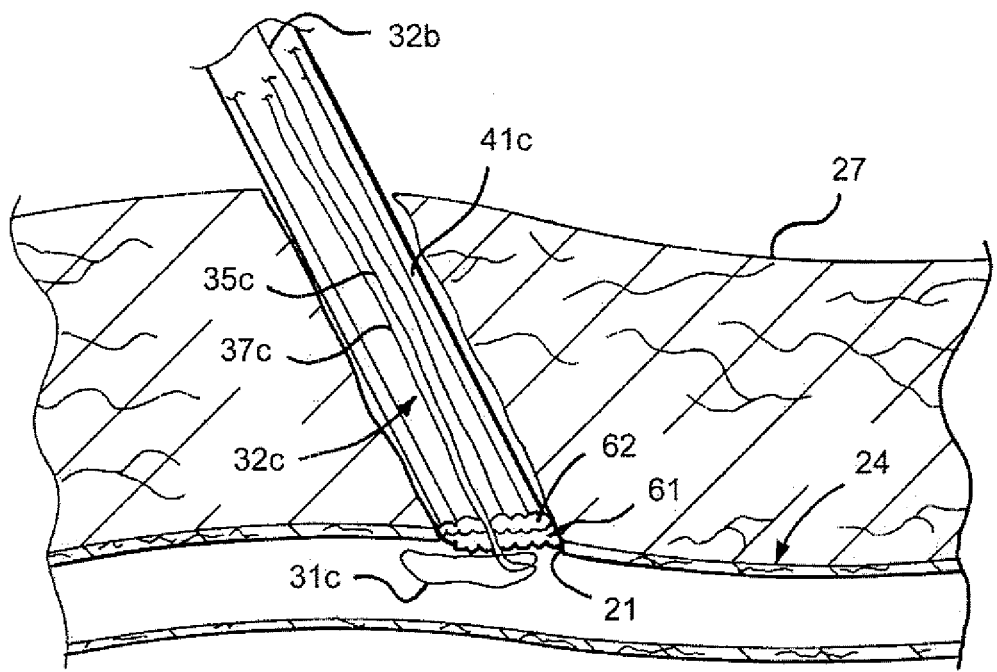
FIG. 15 is a sectional view of a portion of a body, illustrating a catheter and vessel opening orientation indicating device extending through a puncture that extends transdermally into the vessel and that is equipped with one or more plugs for sealing the vessel opening.

Turning to FIG. 15, as an alternative to a suturing mechanism, the outer tube 41c may accommodate one or more plugs 61, 62 along with the wire foot 31c and shaft 32c (as shown by the wire shaft sections 35c, 37c). An additional shaft 32d may be employed to hold the plugs 61, 62 in place as the outer tube 41c is withdrawn or it may be used to push the plugs 61 to 62 outward into position in the vessel opening 21

Figure 16:
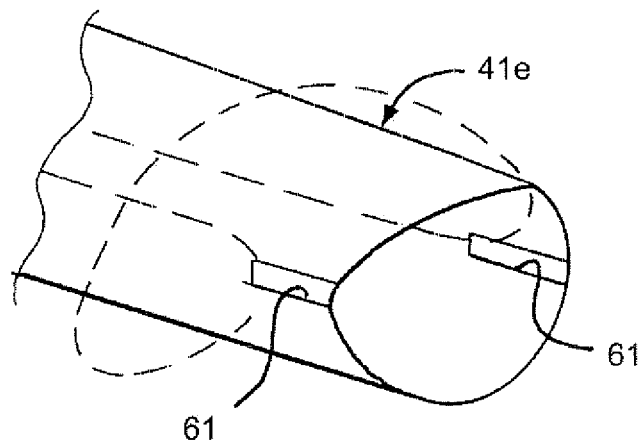
FIG. 16 is a partial perspective view of an end of the tube with diametrically opposed to slots for accommodating hook-shaped needles and/or a vessel opening orientation indicating device made in accordance with this disclosure.
Figure 17:
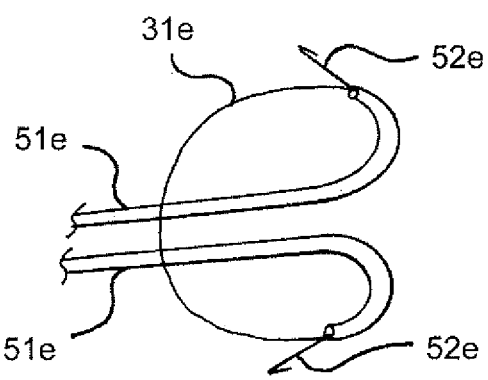
FIG. 17 is a partial view of two hook-shaped needles connected to a loop or foot for indicating the orientation of the vessel opening.

FIG. 16 is an end perspective view of an outer tube 41e equipped with diametrically opposed slot 61 for holding tips of hook-shaped needles 51e as shown in FIG. 17 that are connected to a foot member 31e for purposes of linking the foot member 31e to the tube 41e. The needles 51e may be threaded as indicated by the threads 52e. The slots 61 in FIG. 16 allows the tube 41e to extend into the vessel opening to seal the opening. However, if this technique is employed, it is necessary for the tube 41e to rotate with the foot 31e. Hence, the slots 61 couple the tube 41e to the foot 31e. In the other embodiments disclosed above, the tube 41 could be used to seal the vessel opening but it would not rotate as only the foot 31 and shaft 32 would rotate.

While the drawings show the foot 31 extending primarily at the heel of the opening 21, the foot 31 could extend in both proximal and distal directions in the vessel 24, and does not need to be symmetric in proximal and distal directions. It is preferred that the foot 31 be symmetric in the "right"-"left" directions so that it can rotate equally easily in either direction to indicate orientation While only certain embodiments have been set forth, alternatives and modifications will be apparent from the above description to those skilled in the art. These and other alternatives are considered equivalents and within the spirit and scope of this disclosure and the appended claims

What is claimed is:

1. A device for determining an orientation of an opening in a vessel, the device comprising:
   an outer tube;
   a collapsible foot slidably disposed within a distal end of the outer tube; and
   the foot being connected to a shaft, the shaft passing through the tube and exiting a proximal end thereof, the foot being pushable distally out of the tube and through the opening in the vessel whereupon the foot expands, and
   wherein pulling on the expanded foot in the proximal direction against the vessel provides an indication as to whether the opening in the vessel is in a top stick position, a left stick position or a right stick position.

2. The device of claim 1, wherein the foot has a shape selected from the group consisting of heart-shaped, triangular-shaped, star-shaped, oval-shaped and pear-shaped.

3. The device of claim 1, wherein the foot and shaft are made from a single piece of wire.

4. The device of claim 3, wherein the foot may be re-collapsed after bleeding through the opening is controlled and the foot and shaft may be removed.

5. The device of claim 3, wherein the wire comprises a first proximal end connected to a first shaft section connected to the foot that is connected to a second shaft section terminating at a second proximal end.

6. The device of claim 1, wherein the shaft is connected to an indicator bar with indicia marked thereon for indicating a first position of the foot when the opening is disposed on a left side of the vessel, a second position of the foot when the opening is disposed on a top of the vessel and a third position of the foot when the opening is disposed on a right side of the vessel.

7. The device of claim 6, wherein the tube has a window disposed toward a proximal end thereof and the indicator bar is positioned in alignment with the window so the indicia can be seen through the window.

8. The device of claim 1, wherein the tube accommodates a suturing mechanism.

9. The device of claim 8, wherein the suturing mechanism comprises a plurality of threaded hook needles.

10. The device of claim 1, wherein the tube accommodates a plug for closing the opening.

11. The device of claim 10, wherein the tube further accommodates a shaft for moving the plug distally toward the opening or for holding the plug in position as the tube is withdrawn.

12. A device for determining an orientation of an opening in a vessel and for closing the vessel, the device comprising:
    an outer tube;
    a collapsible foot slidably disposed within a distal end of the outer tube, the foot being connected to a first shaft, the first shaft passing through the tube and exiting a proximal end thereof; and
    a threaded suture needle, the needle being connected to a second shaft, the foot being pushable distally out of the tube and through the opening in the vessel whereupon the foot expands, and
    wherein pulling on the expanded foot in the proximal direction against the vessel provides an indication as to whether the opening in the vessel is in a top stick position, a left stick position or a right stick position.

13. The device of claim 12, wherein the foot is heart shaped.

14. The device of claim 12, wherein the foot and first shaft are made from a single piece of wire.

15. The device of claim 14, wherein the foot may re-collapsed after bleeding through the opening is controlled and the foot and first shaft may be removed.

16. The device of claim 15, wherein the wire comprises a first proximal end connected to a first shaft section connected to the foot that is connected to a second shaft section terminating at a second proximal end.

17. The device of claim 12,
    wherein the first shaft is connected to an indicator bar with indicia marked thereon for indicating a first position of the foot when the opening is disposed on a left side of the vessel, a second position of the foot when the opening is disposed on a top of the vessel and a third position of the foot when the opening is disposed on a right side of the vessel; and
    wherein the tube has a window disposed toward a proximal end thereof and the indicator bar is positioned in alignment with the window so the indicia can be seen through the window.

18. A device for determining an orientation of an opening in a vessel and for closing the vessel, the device comprising:
    an outer tube;
    a collapsible foot slidably disposed within a distal end of the outer tube, the foot being connected to a first shaft, the first shaft passing through the tube and exiting a proximal end thereof; and
    a biodegradable plug connected to a second shaft, wherein the foot may be pushed distally out of the tube and through the opening in the vessel whereupon the foot expands, and
    wherein pulling on the expanded foot in the proximal direction provides an indication as to whether the opening in the vessel is in a top stick position, a left stick position or a right stick position.

19. The device of claim 18, wherein the foot is heart shaped.

20. The device of claim 18, wherein the foot and first shaft are made from a single piece of wire.

21. The device of claim 20, wherein the foot may be re-collapsed after bleeding through the opening is controlled and the foot and shaft may be removed.

22. The device of claim 20, wherein the wire comprises a first proximal end connected to a first shaft section connected to the foot that is connected to a second shaft section terminating at a second proximal end.

23. The device of claim 18, wherein the first shaft is connected to an indicator bar with indicia marked thereon for indicating a first position of the foot when the opening is disposed on a left side of the vessel, a second position of the foot when the opening is disposed on a top of the vessel and a third position of the foot when the opening is disposed on a right side of the vessel, and wherein the tube has a window disposed toward a proximal end thereof and the indicator bar is positioned in alignment with the window so the indicia can be seen through the window.

* * * * *